(12) United States Patent
Shiota et al.

(10) Patent No.: US 10,934,235 B2
(45) Date of Patent: Mar. 2, 2021

(54) METHOD OF PURIFYING (Z)-1-CHLORO-2,3,3,3-TETRAFLUORO PROPENE

(71) Applicant: AGC INC., Chiyoda-ku (JP)

(72) Inventors: Hidefumi Shiota, Chiyoda-ku (JP); Shoji Furuta, Chiyoda-ku (JP)

(73) Assignee: AGC INC., Chiyoda-ku (JP)

( * ) Notice: Subject to any disclaimer, the term of this patent is extended or adjusted under 35 U.S.C. 154(b) by 0 days.

(21) Appl. No.: 16/874,732

(22) Filed: May 15, 2020

(65) Prior Publication Data

US 2020/0277245 A1    Sep. 3, 2020

Related U.S. Application Data

(63) Continuation of application No. PCT/JP2018/042532, filed on Nov. 16, 2018.

(30) Foreign Application Priority Data

Nov. 20, 2017   (JP) .............................. JP2017-222623

(51) Int. Cl.
*C07C 17/383*    (2006.01)
*C07C 17/386*    (2006.01)
*C07C 21/18*    (2006.01)

(52) U.S. Cl.
CPC .......... *C07C 17/383* (2013.01); *C07C 17/386* (2013.01); *C07C 21/18* (2013.01)

(58) Field of Classification Search
CPC ..... C07C 17/386; C07C 17/383; C07C 21/18; C07C 19/10
See application file for complete search history.

(56) References Cited

U.S. PATENT DOCUMENTS

| 2017/0320798 A1 | 11/2017 | Shimokawa et al. |
| 2018/0297918 A1 | 10/2018 | Taniguchi et al. |
| 2019/0161661 A1 | 5/2019 | Tasaka et al. |

FOREIGN PATENT DOCUMENTS

| WO | WO 2016/080283 A1 | 5/2016 |
| WO | WO 2017/110851 A1 | 6/2017 |
| WO | WO 2018/021275 A1 | 2/2018 |

OTHER PUBLICATIONS

International Search Report dated Jan. 29, 2019 in PCT/JP2018/042532 filed Nov. 16, 2018, 1 page.

*Primary Examiner* — Jafar F Parsa
(74) *Attorney, Agent, or Firm* — Oblon, McClelland, Maier & Neustadt, L.L.P.

(57) ABSTRACT

The method of purifying 1224yd (Z) includes: distilling a composition comprising 1224yd (Z) and 244bb in a presence of an extracting solvent comprising at least one compound selected from the group consisting of an alcohol, an ether, a nitrile, a ketone, a carbonate ester, an amide, an ester, a sulfoxide, a hydrocarbon, a chlorohydrocarbon, and a fluorohydrocarbon; and thereby, separating at least a part of 244bb from the composition.

12 Claims, No Drawings

METHOD OF PURIFYING (Z)-1-CHLORO-2,3,3,3-TETRAFLUORO PROPENE

CROSS-REFERENCE TO RELATED APPLICATIONS

This application is a Continuation Application of International Application No. PCT/JP2018/042532, filed Nov. 16, 2018, the disclosure of which is incorporated herein by reference in its entirety. Further, this application claims priority from Japanese Patent Application No. 2017-222623, filed Nov. 20, 2017, the disclosure of which is incorporated herein by reference in its entirety.

TECHNICAL FIELD

The present invention relates to a method of purifying (Z)-1-chloro-2,3,3,3-tetrafluoropropene.

BACKGROUND ART

Hydrochlorofluorocarbon (HCFC) has a negative impact on the ozone layer, and therefore, the production of HCFC is planned to be subject to regulation. HCFC includes, for example, 3,3-dichloro-1,1,1,2,2-pentafluoropropane (HCFC-225ca), or 1,3-dichloro-1,1,2,2,3-pentafluoropropane (HCFC-225cb); however, in view of the regulation on the HCFC, development of compounds that replace HCFC is being anticipated.

Examples of a compound that replaces HCFC include 1-chloro-2,3,3,3-tetrafluoropropene (HCFO-1224yd, hereinafter also simply referred to as "1224yd"). 1224yd is a novel compound which has a low global warming potential (GWP), and which is useful for as a cleaning agent, a solvent, a refrigerant, a blowing agent, and aerosol.

Known methods of producing 1224yd include a method in which 2,3,3,3-tetrafluoropropene (HFO-1234yf; hereinafter, also simply referred to as "1234yf") is reacted with chlorine to produce 1,2-dichloro-2,3,3,3-tetrafluoropropane (HCFC-234bb; hereinafter also simply referred to as "234bb"), followed by a dehydrochlorination reaction of 234bb in a liquid phase in the presence of a base to yield 1224yd (for example, see Patent Literature 1).

In the above method, components of the reaction mixture resulting from the above process, other than the target substance, 1224yd, such as unreacted starting materials, intermediate products, or by-products, are separated by distillation or the like to obtain a high concentration of 1224yd. However, in a case in which a by-product whose boiling point is highly close to that of 1224yd is contained as a component other than 1224yd, it is extremely difficult to separate it with ordinary distillation. As a method of separating components having boiling points that are extremely close to each other, a method called extractive distillation is known. Extractive distillation is a method for separating one of the components from a mixture containing two components having boiling points that are extremely close to each other, or from an azeotropic or near-azeotropic composition containing two components, by adding an extracting solvent that alters the relative volatility, followed by distillation (for example, see Patent Literature 2).

CITATION LIST

Patent Literature

[Patent Literature 1] International Publication No. WO 2017/110851
[Patent Literature 2] International Publication No. WO 2016/080283

SUMMARY OF INVENTION

Technical Problem

The inventors found that, in the reaction mixture obtained in the method of producing 1224yd using 1234yf as a starting material, 2-chloro-1,1,1,2-tetrafluoropropane (HCFC-244bb; hereinafter also simply referred to as "244bb") is contained as a by-product by a reaction between 1234yf and hydrogen chloride generated in the chlorination reaction, in addition to the target substance, 1224yd.

1224yd has a Z-isomer and an E-isomer, and since the Z-isomer is more stable than the E-isomer, there is particularly a need for a method of purifying 1224yd (Z). However, the boiling points of 1224yd (Z) and 244bb are highly close, and for example, the boiling point of 1224yd (Z) is about from 14 to 15° C., and the boiling point of 244bb is about 15.2° C. (both under atmospheric pressure). Therefore, it was found that, when 244bb is remaining in a reaction mixture containing 1224yd (Z), it is extremely difficult to separate 1224yd (Z) and 244bb by a general method such as distillation. Further, in industrially applying extractive distillation for separating 1224yd (Z) and 244bb, selection of the extracting solvent is the most important factor, and further, optimization of distillation conditions is required for each extracting solvent.

As described above, the difference between the boiling point of 1224yd (Z) and that of 244bb is only about 0.2 to 1.2° C. Therefore, conditions relating to the separability of 1224yd (Z) and 244bb are extremely stringent compared to those of ordinary extractive distillation. Therefore, it is extremely difficult to predict what kind of extracting solvent should be used in order to obtain a high concentration of 1224yd (Z) by separating 1224yd (Z) and 244bb efficiently in a mixture containing the two, such as using a distillation column with a small number of plates.

The invention relates to providing a method of purifying 1224yd (Z) by which a purified product of 1224yd (Z) containing a high concentration of 1224yd (Z) can be obtained by efficiently separating 244bb from a composition containing 1224yd (Z) and 244bb.

Solution to Problem

The invention provides a method of purifying (Z)-1-chloro-2,3,3,3-tetrafluoropropene, the method having the following configuration.

[1] A method of purifying (Z)-1-chloro-2,3,3,3-tetrafluoropropene (1224yd (Z)), the method comprising:

distilling a composition comprising (Z)-1-chloro-2,3,3,3-tetrafluoropropene (1224yd (Z)) and 2-chloro-1,1,1,2-tetrafluoropropane (244bb) in a presence of an extracting solvent comprising at least one compound selected from the group consisting of an alcohol, an ether, a nitrile, a ketone, a carbonate ester, an amide, an ester, a sulfoxide, a hydrocarbon, a chlorohydrocarbon, and a fluorohydrocarbon; and thereby, separating at least a part of 244bb from the composition.

[2] The purification method according to [1], wherein a ratio of a molar amount of 1224yd (Z) to a total molar amount of 1224yd (Z) and 244bb in the composition is from 1 to 99% by mole.

[3] The purification method according to [1] or [2], wherein the extracting solvent has a boiling point of from 40° C. to 250° C.

[4] The purification method according to any one of [1] to [3], wherein a molar ratio of the extracting solvent to 244bb is from 0.1:1 to 1000:1.

[5] The purification method according to any one of [1] to [4], wherein the extracting solvent is a solvent that renders the relative volatility of 1224yd (Z) with respect to 244bb larger than 1.

[6] The purification method according to any one of [1] to [4], wherein the extracting solvent is a solvent that renders the relative volatility of 1224yd (Z) with respect to 244bb 1.01 or higher.

[7] The purification method according to any one of [1] to [4], wherein the extracting solvent is a solvent that renders the relative volatility of 1224yd (Z) with respect to 244bb lower than 1.

[8] The purification method according to any one of [1] to [4], wherein the extracting solvent is a solvent that renders the relative volatility of 1224yd (Z) with respect to 244bb 0.96 or lower.

[9] The purification method according to any one of [1] to [4], wherein the extracting solvent is at least one compound selected from the group consisting of $CF_3CH_2OCF_2CF_2H$, $CF_3CF_2CF_2CF_2CF_2CF_2H$, 1,2-dichloro-2,3,3,3-tetrafluoropropane, and 1,3-dichloro-1,1,2,2,3-pentafluoropropane.

[10] The purification method according to any one of [1] to [4], wherein the extracting solvent is at least one compound selected from the group consisting of $CF_3CH_2OCF_2CF_2H$, $CF_3CF_2CF_2CF_2CF_2CF_2H$, and 1,2-dichloro-2,3,3,3-tetrafluoropropane.

[11] The purification method according to any one of [1] to [4], wherein the extracting solvent is at least one compound selected from the group consisting of N,N-dimethylformamide, tetrahydrofuran, acetone, ethyl acetate, toluene, acetonitrile, carbon tetrachloride, methanol, trichloroethylene, chloroform, n-hexane, and 1,1-dichloro-2,3,3,3-tetrafluoropropene.

[12] The purification method according to any one of [1] to [4], wherein the extracting solvent is at least one compound selected from the group consisting of N, N-dimethylformamide, tetrahydrofuran, acetone, ethyl acetate, toluene, acetonitrile, carbon tetrachloride, and methanol.

"Extractive distillation" herein means a distillation operation in which an extracting solvent is added to a composition containing two components having boiling points that are highly close, or two components forming azeotoropic or near-azeotropic composition, the two components having a relative volatility of around 1 and being hardly be able to be separated from each other by ordinary distillation, the extracting solvent rendering the relative volatility between the original two components sufficiently deviate from 1 to facilitate the separation. The solvent alters the original relative volatility between the two components by affecting the vapor-liquid equilibrium relationship.

Herein, a relative volatility of 1224yd (Z) with respect to 244bb represented by the following formula is used to describe a "relative volatility".

Relative volatility of 1224yd (Z) with respect to 244bb= [Molar fraction (%) of 1224yd (Z) in vapor phase/Molar fraction (%) of 244bb in vapor phase]/[Molar fraction (%) of 1224yd (Z) in liquid phase/Molar fraction (%) of 244bb in liquid phase]

Herein, a "top product (distillate)" means a substance distilled out from the top of a distillation column, and a "bottom product (residual)" means a substance discharged from the bottom of the distillation column.

Further, the term "main component" herein means that the amount of components other than the "main component" is relatively small. 50% by mole or more of the total amount suffices as the amount of the "main component", and in particular, the amount of the "main component" is 60% by mole or more, for example, 80% by mole or more. Further, a boiling point of a compound herein is a value at normal pressure ($1.013 \times 10^5$ Pa), unless otherwise specified. Herein, a numerical range expressed by "x to y" includes the values of x and y in the range as a minimum value and a maximum value, respectively.

With respect to halogenated carbons herein, abbreviations of the compounds are denoted in parentheses following the compound names, and the abbreviations may be used in place of the compound names as necessary. Further, with respect to a compound that has a double bond in the molecule thereof and has an E-isomer and a Z-isomer, the E-isomer and the Z-isomer are represented as (E) or (Z) denoted at the end of the abbreviations. When no specific notation is provided with respect to the E-isomer or Z-isomer in the name of a compound or an abbreviation thereof, the name or abbreviation is a collective term encompassing an E-isomer and a Z-isomer as well as a mixture of the E-isomer and the Z-isomer. Further, there may be cases in which only a portion including numbers and lowercase alphabets after a hyphen (-) is used as an abbreviation.

Advantageous Effects of Invention

By the purification method according to the invention, a purified product of 1224yd (Z) containing a high concentration of 1224yd (Z) can be obtained by efficiently separating 244bb from a composition containing 1224yd (Z) and 244bb.

DESCRIPTION OF EMBODIMENTS

Embodiments of the invention will be described below in detail; however, the invention is not limited to the following embodiments.

The method of purifying 1224yd (Z) according to an embodiment includes distilling a composition including 1224yd (Z) and 244bb in a presence of an extracting solvent including at least one compound selected from the group consisting of an alcohol, an ether, a nitrile, a ketone, a carbonate ester, an amide, an ester, a sulfoxide, a hydrocarbon, a chlorohydrocarbon, and a fluorohydrocarbon; and thereby, separating at least a part of 244bb from the composition. The "composition containing 1224yd (Z) and 244bb" is hereinafter also referred to as "composition for distillation".

The boiling points of 1224yd (Z) and 244bb are highly close to each other. Further, 1224yd (Z) and 244bb form an azeotropic composition or near-azeotrope composition almost throughout the entire compositional range. Specifically, with regard to 1224yd (Z) and 244bb, the relative volatility is 1.00±0.01 in a composition in which the content ratio of 1224yd (Z) is from 99 to 1% by mole and the content ratio of 244bb is from 1 to 99% by mole with respect to the total amount of 1224yd (Z) and 244bb. The boiling point of the mixture of 1224yd (Z) and 244bb in the above compositional range is 15.0° C. at $1.011 \times 10^6$ Pa.

An azeotropic composition is a composition in which the relative volatility of 1224yd (Z) with respect to 244bb as defined above is 1. An azeotropic composition is defined as a composition in which a vapor phase generated by vaporization of a liquid phase has the same composition as that of the liquid phase, or in which a liquid phase generated by condensation of a vapor phase has the same composition as that of the vapor phase. The composition of an azeotropic composition does not change by evaporation or condensation. However, the composition of an azeotropic composition varies depending on the pressure conditions.

A near-azeotropic composition is a composition in which the relative volatility of 1224yd (Z) with respect to 244bb as defined above is very close to 1. A near-azeotropic composition behaves similarly to an azeotropic composition. In other words, in a near-azeotropic composition, a vapor phase generated by vaporization of a liquid phase has almost the same composition as that of the liquid phase, or a liquid phase generated by condensation of a vapor phase has almost the same composition as that of the vapor phase.

In the case of an azeotropic composition, i.e., when the relative volatility is 1, separation by distillation is impossible since the composition of the vapor phase and that of the liquid phase are identical. In the case of a near-azeotropic composition, the closer the relative volatility is to 1, the more difficult the separation by distillation is.

In the method of purifying 1224yd (Z) according to this embodiment, an extracting solvent that renders the relative volatility of 1224yd (Z) with respect to 244bb larger than 1 or an extracting solvent that renders the relative volatility lower than 1 is used for separating at least a part of 244bb from the composition for distillation by extractive distillation, thereby obtaining a purified product of 1224yd (Z) containing 1224yd (Z) at a higher concentration. In other words, by using a solvent having a high miscibility with one of 244bb and 1224yd (Z) so as to render one of 1224yd (Z) and 244bb less volatile, the content ratio of 1224yd (Z) with respect to the total amount of 1224yd (Z) and 244bb in the top product or the bottom product after distillation becomes higher than the content ratio of 1224yd (Z) with respect to the total amount of 1224yd (Z) and 244bb in the composition for distillation.

Specifically, when an extracting solvent that renders the relative volatility of 1224yd (Z) with respect to 244bb larger than 1 is used, the molar fraction of 1224yd (Z) in the vapor phase becomes larger, and consequently, in extractive distillation, a portion having a higher content ratio of 1224yd (Z) with respect to the total amount of 1224yd (Z) and 244bb compared to the composition for distillation can be readily obtained as a top product, and a portion having a higher content ratio of 244bb with respect to the total amount of 1224yd (Z) and 244bb compared to the composition for distillation can be readily obtained as a bottom product. Conversely, when an extracting solvent that renders the relative volatility of 1224yd (Z) with respect to 244bb lower than 1 is used, the molar fraction of 244bb in the vapor phase becomes larger, and consequently, in extractive distillation, a portion having a higher content ratio of 244bb with respect to the total amount of 1224yd (Z) and 244bb compared to the composition for distillation can be readily obtained as a top product, and a portion having a higher content ratio of 1224yd (Z) with respect to the total amount of 1224yd (Z) and 244bb compared to the composition for distillation can be readily obtained as a bottom product.

As described above, by to the method of purifying 1224yd (Z) according to this embodiment, a purified product of 1224yd (Z) containing a high concentration of 1224yd (Z) can be obtained by distilling a composition for distillation in the presence of the above-described extracting solvent.

(Composition for Distillation)

The composition for distillation contains 1224yd (Z) and 244bb. The composition for distillation may consist only of 1224yd (Z) and 244bb. A composition for distillation may contain other component(s) than 1224yd (Z) and 244bb insofar as the effect of the invention is not impaired.

The content of 1224yd (Z) in a composition for distillation is not particularly limited, and is preferably 50% by mass or more, more preferably 70% by mass or more, and still more preferably 80% by mass or more, from the viewpoint of distillation efficiency.

Examples of the composition for distillation according to the embodiment includes, for example, a reacted mixture obtained by a method in which 2,3,3,3-tetrafluoropropene (1234yf) is reacted with chlorine to yield 1,2-dichloro-2,3,3,3-tetrafluoropropane (234bb), followed by dehydrochlorination of 234bb in a liquid phase in the presence of a base to yield 1224yd.

Examples of the component(s) contained in the composition for distillation other than 1224yd (Z) and 244bb include: 1224yd (E) formed besides 1224yd (Z) in the method of producing 1224yd using 1234yf as a starting material; 1234yf, which is an unreacted starting material; and 234bb, which is an intermediate product, as well as 1,1,2-trichloro-2,3,3,3-tetrafluoropropane (HCFC-224ba) and 1,1,1,2-tetrachloro-2,3,3,3-tetrafluoropropane (CFC-214bb), which are by-products generated in the reaction processes. These components other than 1224yd (Z) and 244bb can be separated by an ordinary method such as distillation. Therefore, these components other than 1224yd (Z) and 244bb may be removed to a desired level by a known method, such as ordinary distillation, prior to applying the purification method according to the embodiment, in consideration of distillation efficiency or the like. Alternatively, these components may be separated from 1224yd (Z) or 244bb by a known method such as ordinary distillation after applying the purification method according to the embodiment.

(Extracting Solvent)

The extracting solvent in the embodiment is at least one compound selected from the group consisting of an alcohol, an ether, a nitrile, a ketone, a carbonate ester, an amide, an ester, a sulfoxide, a hydrocarbon, a chlorohydrocarbon, and a fluorohydrocarbon.

Here, an alcohol refers to a compound having at least one alcoholic hydroxy group and not having a halogen atom. An aliphatic alcohol having 1 to 6 carbon atoms in the main chain is preferable, and an aliphatic alcohol having 1 to 4 carbon atoms is more preferable. Specific examples thereof include methanol, ethanol, 1-propanol, 2-propanol, 1-butanol, 2-butanol, 2-methyl-1-propanol, 2-methyl-2-propanol, 1-pentanol, 2-pentanol, 1-ethyl-1-propanol, 2-methyl-1-butanol, 3-methyl-1-butanol, 3-methyl-2-butanol, neopentyl alcohol, 1-hexanol, 2-methyl-1-pentanol, 4-methyl-2-pentanol, and 2-ethyl-1-butanol. Among them, from the viewpoints of availability and productivity in the distillation step, methanol, ethanol, and 2-propanol are preferable, and methanol is most preferable.

An ether refers to a compound having at least one ether bond and not having a halogen atom, and may be cyclic or straight-chain. The number of carbon atoms in the ether is preferably from 1 to 6, and more preferably from 1 to 4. Specific examples thereof include dimethyl ether, diethyl ether, dipropyl ether, diisopropyl ether, ethyl methyl ether, ethyl propyl ether, ethyl isopropyl ether, 1,3-dioxolan, 1,4-dioxane, trimethoxyethane, triethoxyethane, furan, 2-methylfuran, and tetrahydrofuran (THF). Among them, from the viewpoints of availability and productivity in the distillation step, 1,3-dioxolan, 1,4-dioxane, and THF are preferable, and THF is most preferable.

A nitrile refers to a compound represented by a general formula $R^1$—CN (wherein $R^1$ represents an unsubstituted aliphatic hydrocarbon group). As the nitrile, a nitrile represented by the above general formula in which $R^1$ has 1 to 5 carbon atoms is preferable. Specific examples thereof include acetonitrile, propionitrile, butyronitrile, and isobutyronitrile. Among them, acetonitrile is preferable from the viewpoints of availability and productivity in the distillation step.

A ketone refers to a compound represented by a general formula $R^2$—C(=O)—$R^3$ (wherein $R^2$ and $R^3$ represent the same or different unsubstituted aliphatic hydrocarbon groups). A ketone represented by the above general formula in which $R^2$ and $R^3$ each has 1 or 2 carbon atoms, and the total number of carbon atoms included in $R^2$ and $R^3$ is from 2 to 4, is preferable. Specific examples thereof include acetone, ethyl methyl ketone, and diethyl ketone. Among them, acetone is preferable from the viewpoints of availability and productivity in the distillation step.

A carbonate ester is preferably a chain carbonate ester having 1 to 6 carbon atoms and an aliphatic cyclic carbonate ester having 1 to 6 carbon atoms. Specific examples thereof include dimethyl carbonate, diethyl carbonate, ethylene carbonate, and propylene carbonate. Among them, dimethyl carbonate and diethyl carbonate are preferable from the viewpoints of availability and productivity in the distillation step.

Examples of an amide include a chain amide having 3 to 5 carbon atoms and an aliphatic cyclic amide having 3 to 5 carbon atoms, and a tertiary amide in which all of the hydrogen atoms of the amino group are substituted with an alkyl group is preferable. Specific examples thereof include formamide, acetamide, N, N-dimethylformamide (DMF), and N, N-dimethylacetamide. Among them, from the viewpoints of availability and productivity in the distillation step, DMF and N, N-dimethylacetamide are preferable, and DMF is most preferable.

An ester refers to a compound which has an ester group other than a carbonate ester. Examples of the ester include a chain ester having 3 to 6 carbon atoms and an aliphatic cyclic ester having 3 to 6 carbon atoms, and a chain ester having 4 to 6 carbon atoms is preferable. Specific examples of the ester include methyl acetate, ethyl acetate, propyl acetate, and butyl acetate. Among them, ethyl acetate is preferable from the viewpoints of availability and productivity in the distillation step.

A sulfoxide refers to a compound represented by a general formula $R^4$—S(=O)—$R^5$ (wherein $R^4$ and $R^5$ represent the same or different unsubstituted aliphatic hydrocarbon groups). Specifically, dimethyl sulfoxide (DMSO), which is a compound represented by the above general formula in which $R^4$ and $R^5$ are both methyl groups, is preferable from the viewpoints of availability and productivity in the distillation step.

Examples of a hydrocarbon include an aliphatic chain hydrocarbon having 3 to 6 carbon atoms, an aliphatic cyclic hydrocarbon having 3 to 6 carbon atoms, and an aromatic hydrocarbon having 6 to 10 carbon atoms. An aliphatic chain hydrocarbon having 3 to 6 carbon atoms, or an aromatic hydrocarbon having 6 to 10 carbon atoms is preferable. Specific examples thereof include n-pentane, isopentane, n-hexane, cyclohexane, benzene, and toluene. Among them, from the viewpoints of availability and productivity in the distillation step, n-hexane and toluene are preferable, and toluene is most preferable.

A chlorohydrocarbon refers to a compound in which one or more of hydrogen atoms of the hydrocarbon skeleton are substituted with chlorine atom(s), and is a compound having no fluorine atom. The chlorohydrocarbon is preferably a compound having a skeleton of an aliphatic chain hydrocarbon having 1 to 4 carbon atoms or an aliphatic cyclic hydrocarbon having 1 to 4 carbon atoms. Specific examples of the chlorohydrocarbon include dichloromethane, chloroform ($CHCl_3$), carbon tetrachloride ($CCl_4$), 1,2-dichloropropane, perchloroethylene, and trichloroethylene. Among them, from the viewpoints of availability and productivity in the distillation step, chloroform, carbon tetrachloride, and trichloroethylene are preferable, and carbon tetrachloride is most preferable.

A fluorohydrocarbon refers to a compound in which one or more of hydrogen atoms of the hydrocarbon skeleton are substituted with fluorine atoms. The fluorohydrocarbon is preferably a compound having a skeleton of an aliphatic chain hydrocarbon having 1 to 10 carbon atoms or an aliphatic cyclic hydrocarbon having 1 to 10 carbon atoms. The fluorohydrocarbon may have an ether bond or a double bond between/within carbon-carbon bonds. Further, a hydrogen atom of the hydrocarbon skeleton may be substituted with a chlorine atom, a hydroxy group or the like.

Examples of the fluorohydrocarbon not having an ether bond or a double bond between/within carbon-carbon bonds include $CF_3CF_2CF_2CF_2CF_2CF_2CH_2CH_3$ (for example, AC6000 (trade name) produced by AGC Inc.), $CF_3CF_2CF_2CF_2CF_2CF_2H$ (for example, AC2000 (trade name) produced by AGC Inc.), and $CF_3CF_2CHFCHFCF_3$ (for example, HFC4310 (trade name) produced by du Pont de Nemours, Inc.).

Further, examples of the fluorohydrocarbon having a chlorine atom include $CClF_2CF_2CHClF$ (HCFC-225cb), and HCFC-234bb.

Examples of the fluorohydrocarbon having a double bond and a chlorine atom include 1,1-dichloro-2,3,3,3-tetrafluoropropene (CFO-1214ya).

As the fluorohydrocarbon, $CF_3CF_2CF_2CF_2CF_2CF_2CH_2CH_3$, $CF_3CF_2CF_2CF_2CF_2CF_2H$, HCFC-225cb, HCFC-234bb, and CFO-1214ya are preferable from the viewpoints of availability and productivity in the distillation step.

As the fluorohydrocarbon having an ether bond between/within carbon-carbon bonds, $CF_3CH_2OCF_2CF_2H$ (for example, AE3000 (trade name) produced by AGC Inc.), tetrafluoropropanol, $CF_3CF_2CF_2CF_2OCF_3$ (for example, NOVEC 7100 (trade name) produced by Sumitomo 3M Ltd.), $CF_3CF_2CF_2CF_2OCH_2CH_3$ (for example, NOVEC 7200 (trade name) produced by Sumitomo 3M Ltd.), $CF_3CF_2CF(CH_3)OCF(CF_3)_2$ (for example, NOVEC 7300 (trade name) produced by Sumitomo 3M Ltd.), the compound represented by Formula (1) (for example, FC-77 (trade name) produced by Sumitomo 3M Ltd.), a compound represented by Formula (2) (for example, SV-55 (trade name) produced by Solvay S.A.), and a compound represented by Formula (3) (for example, HT-70, HT-80, HT-110, or HT-135 (trade names) produced by Solvay S.A.) are preferable from the viewpoints of availability and productivity in the distillation step.

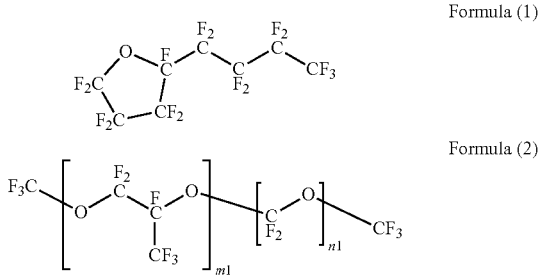

Formula (1)

Formula (2)

In Formula (2), m1 and n1 are integers of 1 to 20.

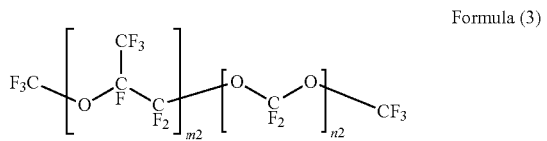

Formula (3)

In Formula (3), m2 and n2 are integers of 1 to 20.

Among the above listed compounds, an extracting solvent having a boiling point of from 40 to 250° C. is preferable, and an extracting solvent having a boiling point of from 40 to 160° C. is more preferable. When the boiling point of the extracting solvent is within the above range, productivity in the distillation step can be even superior. When a mixed solvent containing two or more compounds is used as an extracting solvent, the boiling point of the mixed solvent is preferably in the above range.

The extracting solvents may be classified into a solvent that has a miscibility only with 244bb out of 1224yd (Z) and 244bb, thereby rendering 244bb less volatile, and rendering the relative volatility of 1224yd (Z) with respect to 244bb larger than 1 (hereinafter also referred to as a "first extracting solvent"); and a solvent that has a miscibility only with 1224yd (Z) out of 1224yd (Z) and 244bb, thereby rendering 1224yd (Z) less volatile, and rendering the relative volatility of 1224yd (Z) with respect to 244bb lower than 1 (hereinafter also referred to as a "second extracting solvent").

The first extracting solvent is preferably capable of rendering the relative volatility of 1224yd (Z) with respect to 244bb about 1.01 or higher, and more preferably 1.02 or higher, the relative volatility of 1224yd (Z) with respect to 244bb being measured by the method described below after adding the extracting solvent to a mixture of 244bb and 1224yd (Z). When the relative volatility of 1224yd (Z) with respect to 244bb is equal to or higher than the above-described lower limit, 1224yd (Z) becomes more volatile.

When a compound having a fluorine atom is used as the extracting solvent, the relative volatility of 1224yd (Z) with respect to 244bb tends to become large. Therefore, for the first extracting solvent, a compound having a fluorine atom, namely the aforedescribed fluorohydrocarbon, is preferable.

For the first extracting solvent, among others, $CF_3CH_2OCF_2CF_2H$ (for example, AE3000), $CF_3CF_2CF_2CF_2CF_2H$ (for example, AC2000), HCFC-234bb, or HCFC-225cb is preferable; $CF_3CH_2OCF_2CF_2H$, $CF_3CF_2CF_2CF_2CF_2H$, or HCFC-234bb is more preferable; and $CF_3CH_2OCF_2CF_2H$, or $CF_3CF_2CF_2CF_2CF_2H$ is most preferable, from the viewpoint of efficiently separating 244bb and 1224yd (Z). The first extracting solvent may consist of one of the above, and may contain two or more kinds thereof as necessary.

The second extracting solvent is preferably capable of rendering the relative volatility of 1224yd (Z) with respect to 244bb about 0.98 or lower, more preferably to 0.96 or lower, and further preferably to 0.90 or lower, the relative volatility of 1224yd (Z) with respect to 244bb being measured by the method described below after adding the extracting solvent to a mixture of 244bb and 1224yd (Z). When the relative volatility of 1224yd (Z) with respect to 244bb is equal to or less than the aforedescribed lower limit, 244bb vaporizes more easily.

When a compound not having a fluorine atom is used as the extracting solvent, the relative volatility of 1224yd (Z) with respect to 244bb tends to become low. Therefore, for the second extracting solvent, a compound not having a fluorine atom, that is, an alcohol, an ether, a nitrile, a ketone, a carbonate ester, an amide, an ester, a sulfoxide, a hydrocarbon, or a chlorohydrocarbon, among those listed above, is preferable. An alcohol, an ether, a nitrile, a ketone, an amide, an ester, a sulfoxide, a hydrocarbon, or a chlorohydrocarbon is more preferable.

For the second extracting solvent, from the viewpoint of separating 244bb and 1224yd (Z) efficiently, DMF, THF, acetone, ethyl acetate, toluene, acetonitrile, carbon tetrachloride, methanol, trichloroethylene, chloroform, n-hexane or CFO-1214ya is preferable, DMF, THF, acetone, ethyl acetate, toluene, acetonitrile, carbon tetrachloride, or methanol is more preferable, and DMF, THF, acetone, or ethyl acetate is most preferable. The second extracting solvent may consist of one of the above, and may contain two or more kinds thereof.

The value of the relative volatility of 1224yd (Z) with respect to 244bb after the extracting solvent is added to a mixture of 244bb and 1224yd (Z) may be measured as follows. To a mixture of 1224yd (Z) and 244bb at a molar ratio of 5/1, an extracting solvent is added at a molar ratio (extracting solvent/1224yd (Z)/244bb) of 40/50/10 to prepare a test sample. The test sample is placed in a distillation apparatus, and heated gradually with an external heater to bring the test sample to a boil while performing a reflux under atmospheric pressure. After the boiling state is stabilized, the test sample is maintained for a certain period of time so that the composition in the distillation apparatus becomes stable. Next, samples from the vapor phase and the liquid phase of the test sample are collected respectively, and analyzed for the molar ratio of 1224yd (Z) to 244bb using gas chromatography. Then, the relative volatility of 1224yd (Z) with respect to 244bb after addition of the extracting solvent is determined based on the molar ratio of the two.

The amount of the extracting solvent used in the purification method according to the invention is not particularly limited, and the molar ratio of the extracting solvent to 244bb is preferably from 0.1/1 to 1000/1.

(Distillation)

In the purification method according to the invention, extractive distillation may be performed by, using an apparatus generally used for distillation, for example, a distillation column such as a plate column or a packed column, supplying a composition for distillation and an extracting solvent to the distillation column. A distillation column made of carbon steel with an inner lining of at least one of glass, stainless steel, a tetrafluoroethylene resin, a chlorotrifluoroethylene resin, a vinylidene fluoride resin, a tetrafluoroethylene/perfluoroalkoxyethylene copolymer resin or the like may be used.

Either the composition for distillation or the extracting solvent may be supplied earlier to the distillation column, and the both may be supplied simultaneously, insofar as the composition for distillation is distilled in the distillation column in the presence of the extracting solvent. For example, an extracting solvent may be added to the composition for distillation, which may be then supplied to the distillation column. However, from the viewpoint of the efficiency of the distillation operation, it is preferable that the composition for distillation be brought into contact with the extracting solvent in the distillation column, such as by supplying the extracting solvent to the distillation column in which the composition for distillation has been supplied, whereby the distillation is initiated immediately upon mixing.

Various conditions of extractive distillation, such as the operating temperature, the operating pressure, reflux ratio, the total plate number of the distillation column, locations of feed plates, and the location of a feed plate for the extracting solvent, are not particularly limited, and may be selected as necessary in order to accomplish desired separation. Since both 1224yd (Z) and 244bb have low boiling points, it is preferable to perform extractive distillation under an elevated pressure, for example at 0 to $5 \times 10^6$ Pa (gauge pressure), preferably at 0 to $3 \times 10^6$ Pa, in particular at 0 to $2 \times 10^6$ Pa.

Further, the temperatures of the top and the bottom sections of the distillation column depends on the operating pressure and the compositions of the top product and the bottom product. In order to perform the distillation operation in an economical manner, taking into account the temperatures of the condenser and the reboiler provided at the top and the bottom sections, the temperature of the top section is preferably from −60 to 100° C., and the temperature of the bottom section is preferably from 50 to 200° C. Although extractive distillation may be performed batchwise, in a continuous manner, or in a semi-continuous manner as necessary in which the top product and the bottom product are intermittently removed, or in which the composition for distillation is intermittently supplied, the extracting solvent is preferably supplied to the distillation column continuously.

The first extracting solvent renders the relative volatility of 1224yd (Z) with respect to 244bb larger than 1. Therefore, when extractive distillation is conducted on a mixture for distillation containing 1224yd (Z), 244bb and a first extracting solvent, a top product in which the content ratio of 1224yd (Z) with respect to the total amount of 1224yd (Z) and 244bb is higher than in the composition for distillation, or preferably a top product containing 1224yd (Z) as a main component, may be obtained from the top of the distillation column.

The composition of the top product is not particularly limited, insofar as the content ratio of 1224yd (Z) with respect to the total amount of 1224yd (Z) and 244bb is higher than in the composition for distillation, or preferably 1224yd (Z) is contained as a main component. The molar fraction (%) of 1224yd (Z) with respect to the total amount of 1224yd (Z) and 244bb in the top product is preferably 90% by mole or more. Since the first extracting solvent is contained in the top product, further distillation may be conducted to obtain a purified product of 1224yd (Z) containing a higher concentration of 1224yd (Z).

Further, a bottom product containing 244bb can be obtained from the bottom of a distillation column. Although 1224yd (Z) is also contained in the bottom product, the molar fraction of 1224yd (Z) with respect to the total amount of 1224yd (Z) and 244bb is remarkably lower than the molar fraction of 1224yd (Z) with respect to the total amount of 1224yd (Z) and 244bb in the composition for distillation. It is preferable that the molar fraction of 1224yd (Z) with respect to the total amount of 1224yd (Z) and 244bb in the bottom product be reduced to equal to or lower than 1/10 of the molar fraction of 1224yd (Z) with respect to the total amount of 1224yd (Z) and 244bb in the composition for distillation.

Further, since the bottom product contains the first extracting solvent, by further distilling the bottom product, extractive distillation described above can be performed again, whereby the molar fraction of 1224yd (Z) with respect to the total amount of 1224yd (Z) and 244bb in the bottom product can be further reduced.

As described above, when the first extracting solvent is used in the embodiment, at least a part of 244bb is efficiently separated from the composition for distillation into the bottom product, and a purified product of 1224yd (Z) in which the content ratio of 1224yd (Z) with respect to the total amount of 1224yd (Z) and 244bb is higher than in the composition for distillation, or preferably in which 1224yd (Z) is contained as a main component, or in other words, 1224yd (Z) is contained at a higher concentration, may be obtained as the top product. Both the first extracting solvent in the bottom product, and the first extracting solvent in the top product can be separated by ordinary distillation.

The second extracting solvent renders the relative volatility of 1224yd (Z) with respect to 244bb lower than 1. Therefore, when extractive distillation is conducted on a mixture for distillation containing 1224yd (Z), 244bb and a second extracting solvent, a top product in which the content ratio of 244bb with respect to the total amount of 1224yd (Z) and 244bb is higher than in the composition for distillation, or preferably a top product containing 244bb as a main component, may be obtained from the top of the distillation column.

Although in this case 1224yd (Z) is also contained in the top product, the molar fraction of 1224yd (Z) with respect to the total amount of 1224yd (Z) and 244bb is remarkably lower than the molar fraction of 1224yd (Z) with respect to the total amount of 1224yd (Z) and 244bb in the composition for distillation. It is preferable that the molar fraction of 1224yd (Z) with respect to the total amount of 1224yd (Z) and 244bb in the top product be reduced to equal to or lower than 1/10 of the molar fraction of 1224yd (Z) with respect to the total amount of 1224yd (Z) and 244bb in the composition for distillation.

Further, since the top product contains the second extracting solvent, by further distilling the top product, extractive distillation described above can be performed again, whereby the molar fraction of 1224yd (Z) with respect to the total amount of 1224yd (Z) and 244bb in the top product can be further reduced.

Further, a bottom product containing 1224yd (Z) can be obtained from the bottom of a distillation column. The content ratio of 1224yd (Z) with respect to the total amount of 1224yd (Z) and 244bb in the bottom product is higher than in the composition for distillation, and preferably, 1224yd (Z) is contained as a main component, and more preferably the molar fraction (%) of 1224yd (Z) with respect to the total amount of 1224yd (Z) and 244bb is 90% by mole or more. Further, since the bottom product contains the second extracting solvent, by further distilling the bottom product, extractive distillation described above can be performed again, whereby the molar fraction of 244bb with respect to the total amount of 1224yd (Z) and 244bb in the bottom product can be further reduced.

As described above, by using the second extracting solvent, 1224yd (Z) is efficiently separated from the composition for distillation into the bottom product. Both the second extracting solvent in the bottom product and the second extracting solvent in the top product can be separated by ordinary distillation.

EXAMPLES

The invention will be specifically described below with reference to examples; however, the invention is not limited to the following examples.

[Analysis Conditions]

In the measurement of relative volatilities described below, composition analysis of the obtained liquids was performed with gas chromatography (GC). The column used was DB-1301 (length 60 m×inner diameter 250 µm×thickness 1 µm; manufactured by Agilent Technologies, Inc.).

[Measurement of Relative Volatilities]

1224yd (Z), 244bb and an extracting solvent were fed to an Othmer type vapor/liquid equilibrium distillation apparatus, followed by heating the composition to a boil (at approximately 50° C.) and performing a reflux under atmospheric pressure. The molar ratio of the extracting solvent, 1224yd (Z) and 244bb was 40/50/10 in each example. The molar ratio of 1224yd (Z) and 244bb without the extracting solvent was 50/10. The heating condition was adjusted such that the dropping rate of the condensate of the vapor phase became appropriate, and the composition was maintained stably boiling for two hours, during which it was confirmed that the pressure and the boiling point were stable.

Thereafter, samples from the liquid phase and vapor phase were collected and analyzed with gas chromatography. Based on the analysis results, the relative volatility of 1224yd (Z) with respect to 244bb was calculated according to the formula of relative volatility described above. Table 1 shows relative volatilities of 1224yd (Z) with respect to 244bb for the mixtures of respective examples each containing 1224yd (Z), 244bb, and an extracting solvents.

TABLE 1

| Extracting Solvent Type | Relative Volatility 1224yd(Z)/244bb |
|---|---|
| None | 0.995 |
| DMF | 0.754 |
| THF | 0.846 |
| Acetone | 0.863 |
| Ethyl acetate | 0.881 |
| Toluene | 0.919 |
| Acetonitrile | 0.924 |
| Carbon tetrachloride | 0.949 |
| Methanol | 0.959 |
| Trichloroethylene | 0.962 |
| Chloroform | 0.964 |
| n-Hexane | 0.975 |
| CFO-1214ya | 0.979 |
| HCFC-225cb | 1.007 |
| HCFC-234bb | 1.011 |
| AC2000 | 1.027 |
| AE3000 | 1.050 |

As shown in table 1, it is demonstrated that AE3000, which is $CF_3CH_2OCF_2CF_2H$; AC2000, which is $CF_3CF_2CF_2CF_2CF_2H$; HCFC-234bb; and HCFC-225cb can be used as first extracting solvents. In other words, it can be understood that, by using the above as extracting solvents, the relative volatility of 1224yd (Z) with respect to 244bb becomes large. Therefore, by performing extractive distillation using these first extracting solvents, a purified product of 1224yd (Z) in which the content ratio of 1224yd (Z) with respect to the total amount of 1224yd (Z) and 244bb is higher than in the composition for distillation, i.e., 1224yd (Z) is contained at a higher concentration, can be obtained as a top product from the top of the distillation column.

It is also demonstrated that DMF, THF, acetone, ethyl acetate, toluene, acetonitrile, carbon tetrachloride, methanol, trichloroethylene, chloroform, n-hexane, and CFO-1214ya can be used as second extracting solvents. In other words, it can be understood that, by using the above as extracting solvents, the relative volatility of 1224yd (Z) with respect to 244bb becomes low. Therefore, by performing extractive distillation using these second extracting solvents, a purified product of 1224yd (Z) in which the content ratio of 1224yd (Z) with respect to the total amount of 1224yd (Z) and 244bb is higher than in the composition for distillation, i.e., 1224yd (Z) is contained at a higher concentration, can be obtained as a bottom product from the distillation column.

The invention claimed is:

1. A method of purifying (Z)-1-chloro-2,3,3,3-tetrafluoropropene, the method comprising:
    distilling a composition comprising (Z)-1-chloro-2,3,3,3-tetrafluoropropene and 2-chloro-1,1,1,2-tetrafluoropropane in a presence of an extracting solvent comprising at least one compound selected from the group consisting of an alcohol, an ether, a nitrile, a ketone, a carbonate ester, an amide, an ester, a sulfoxide, a hydrocarbon, a chlorohydrocarbon, and a fluorohydrocarbon; and
    thereby, separating at least a part of 2-chloro-1,1,1,2-tetrafluoropropane from the composition.

2. The purification method according to claim 1, wherein a ratio of a molar amount of (Z)-1-chloro-2,3,3,3-tetrafluoropropene to a total molar amount of (Z)-1-chloro-2,3,3,3-tetrafluoropropene and 2-chloro-1,1,1,2-tetrafluoropropane in the composition is from 1 to 99% by mole.

3. The purification method according to claim 1, wherein the extracting solvent has a boiling point of from 40° C. to 250° C.

4. The purification method according to claim 1, wherein a molar ratio of the extracting solvent to 2-chloro-1,1,1,2-tetrafluoropropane is from 0.1:1 to 1000:1.

5. The purification method according to claim 1, wherein the extracting solvent is a solvent that renders the relative volatility of (Z)-1-chloro-2,3,3,3-tetrafluoropropene with respect to 2-chloro-1,1,1,2-tetrafluoropropane larger than 1.

6. The purification method according to claim 1, wherein the extracting solvent is a solvent that renders the relative volatility of (Z)-1-chloro-2,3,3,3-tetrafluoropropene with respect to 2-chloro-1,1,1,2-tetrafluoropropane 1.01 or higher.

7. The purification method according to claim 1, wherein the extracting solvent is a solvent that renders the relative volatility of (Z)-1-chloro-2,3,3,3-tetrafluoropropene with respect to 2-chloro-1,1,1,2-tetrafluoropropane lower than 1.

8. The purification method according to claim 1, wherein the extracting solvent is a solvent that renders the relative volatility of (Z)-1-chloro-2,3,3,3-tetrafluoropropene with respect to 2-chloro-1,1,1,2-tetrafluoropropane 0.96 or lower.

9. The purification method according to claim 1, wherein the extracting solvent is at least one compound selected from the group consisting of $CF_3CH_2OCF_2CF_2H$, $CF_3CF_2CF_2CF_2CF_2H$, 1,2-di chloro-2,3,3,3-tetrafluoropropane, and 1,3-dichloro-1,1,2,2,3-pentafluoropropane.

10. The purification method according to claim 1, wherein the extracting solvent is at least one compound selected from the group consisting of $CF_3CH_2OCF_2CF_2H$, $CF_3CF_2CF_2CF_2CF_2CF_2H$, and 1,2-dichloro-2,3,3,3-tetrafluoropropane.

11. The purification method according to claim 1, wherein the extracting solvent is at least one compound selected from the group consisting of N,N-dimethylformamide, tetrahydrofuran, acetone, ethyl acetate, toluene, acetonitrile, carbon tetrachloride, methanol, trichloroethylene, chloroform, n-hexane, and 1,1-dichloro-2,3,3,3-tetrafluoropropene.

12. The purification method according to claim 1, wherein the extracting solvent is at least one compound selected from the group consisting of N, N-dimethylformamide, tetrahydrofuran, acetone, ethyl acetate, toluene, acetonitrile, carbon tetrachloride, and methanol.

* * * * *